United States Patent
de Oliveira

(10) Patent No.: US 6,261,833 B1
(45) Date of Patent: Jul. 17, 2001

(54) TUBE WITH SPECIAL SCALE INTENDED FOR TESTS WHICH ANALYZE SOMATIC CELL COUNT IN MILK

(75) Inventor: Andre Fernando Alves de Oliveira, Jundiai (BR)

(73) Assignee: Madasa Do Brasil Importacao E Exportacao Ltda., Itapeceria Da Serra (BR); a part interest ( * ) Notice: Subject to any disclaimer, the term of this patent is extended or adjusted under 35 U.S.C. 154(b) by 0 days.

(21) Appl. No.: 09/617,084

(22) Filed: Jul. 14, 2000

(30) Foreign Application Priority Data

Jul. 16, 1999 (BR) .............................................. 7901407 U

(51) Int. Cl.$^7$ .................................................... C12M 1/34
(52) U.S. Cl. .......................... 435/288.1; 422/73; 422/74; 422/101
(58) Field of Search ............... 422/73, 74, 101, 422/102; 436/22; 435/288.1

(56) References Cited

U.S. PATENT DOCUMENTS 5,700,645 * 12/1997 Pahuski et al. ......................... 435/6
6,031,367 * 2/2000 Mangan ............................. 324/71.4

FOREIGN PATENT DOCUMENTS 0-476850 A1 * 3/1992 (EP) .

* cited by examiner

Primary Examiner—David A. Redding

(57) ABSTRACT

Tube with special scale intended for tests which analyze somatic cell count in milk, comprising a tube-shaped reservoir 130 mm high and 12.1 mm in diameter (inside)×140 mm (height) (1), closed at its bottom (2) and completely open at its top (3), with a 3-mm hole at a height of 78 mm (4), and having a quickly adjustable and hermetically sealing lid or stopper (8), having a central hole with diameter of 1.09 to 1.10 mm (9), also made of high-density polyethylene plastic material, wherein because a scale graduated in thousands of somatic cells (5) is printed on said tube, for the purpose of indicating in an automatic fashion directly on the tube itself the results of the test for which the tube was intended, said scales starting 5 mm from the bottom of the tube, this being the scale of least value (140 thousand cells per milliliter of milk) (6), the other scales laid out every 5 mm, with the scale of greatest value (2,280 thousand cells per milliliter of milk ) (7), located 40 mm from the bottom of the tube. These divisions or scales are not linear and are the product of a correlation between residual volume and somatic cell count.

2 Claims, 3 Drawing Sheets

Figure 1:
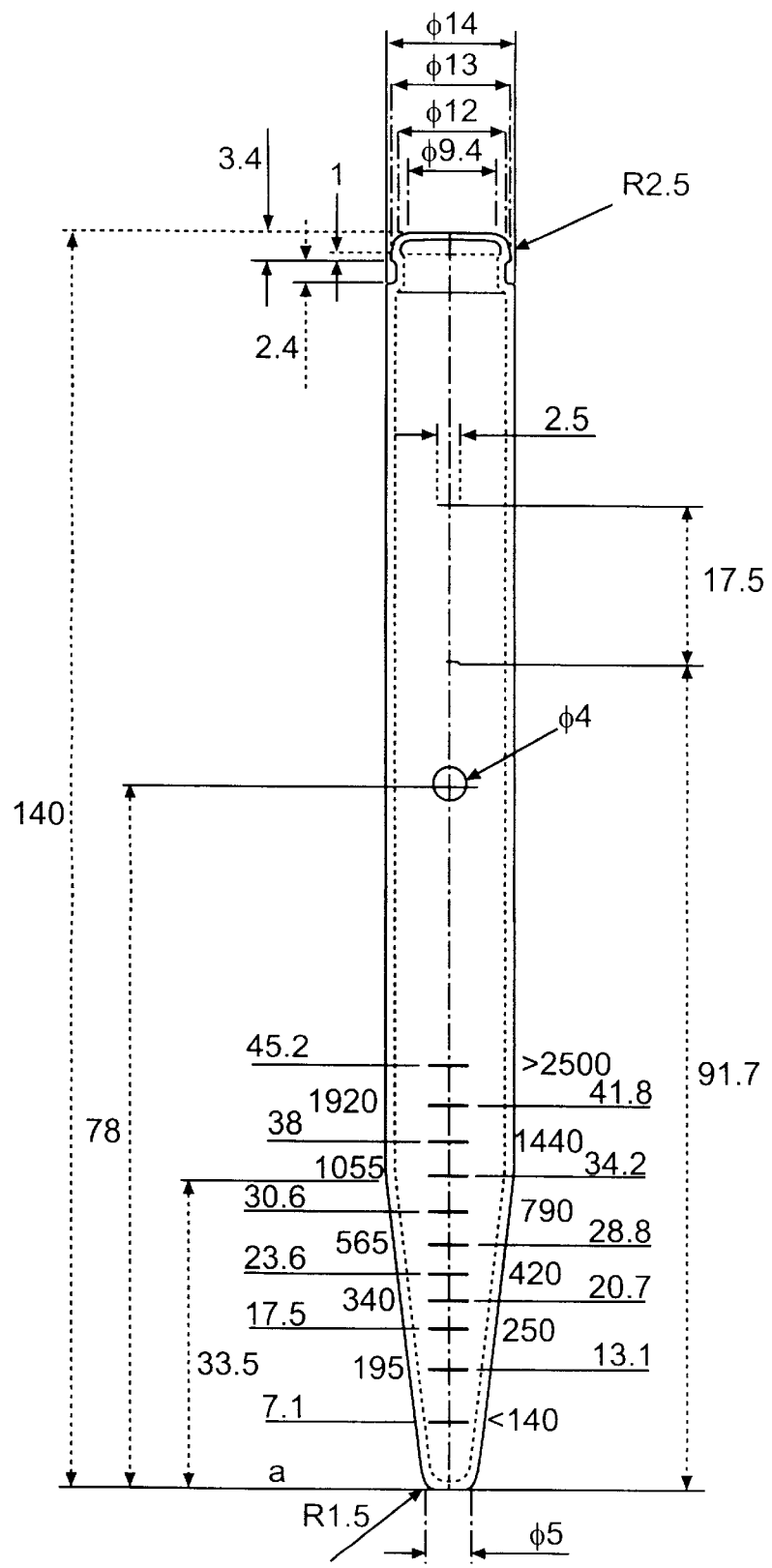

TUBE WITH SPECIAL SCALE INTENDED FOR TESTS WHICH ANALYZE SOMATIC CELL COUNT IN MILK

The object of this utility model is a tube with a scale, intended for tests which analyze milk quality from the perspective of the milk's somatic cell count, for use on farms, milk tankers, in milk processing plants, in sum anywhere milk is handled, which was the aim of the original model, the current aim being to improve its use and effectiveness for tests which analyze somatic cell count in milk, in comparison to known and existing tubes used in these tests.

The test in which the tube in question is used consists of mixing in the tube a sample of milk with a reagent and subsequently inverting this tube, so that this mixture leaks out of the orifice existing in the lid on top of the tube for a certain period of time. When this period of time has elapsed, the amount of mixture remaining in the tube is measured, thereby obtaining the results of the test.

Tubes are already known and used in tests which analyze somatic cell count in milk, said tubes being made of transparent plastic or glass, with a lateral hole in the wall at a certain height to allow air to enter, and an opening in the top of the tube, which is capped with a lid having an orifice in the middle, but which must allow the mixture contained in the tube to drain when the latter is inverted.

Currently used and known tubes have no printed markings on them which directly indicate the results of the test, as these must be examined by measuring the contents remaining in the tube, by placing on the side a separate ruler, which will indicate the data to be analyzed on a suitable table, also separate, which will then indicate the somatic cell count for that milk sample.

Although this type of tube for performing tests which analyze somatic cell count in milk is widely used, these tubes have a number of drawbacks, such as for example the need to transfer the data to a suitable table and use of correlations and conversion factors, examined and measured outside of the tube, which introduces the possibility of error during transfer of the data, and even if this external measurement is done properly, requires a combination of two devices to accomplish its aim (the ruler and the tube).

It was to circumvent these drawbacks—which increase the margin of error of the test for which the tube in question is intended, and which complicate suitable examination of test results—that the tube which is the object of this utility model was developed, said tube having a special scale intended for somatic cell count analysis tests of milk, and said utility model consisting in applying printed graduation marks to the tube which will display the test results directly on the tube, without the need to use external elements, or coordinate and analyze data in a suitable table, since the graduation marks printed on this tube are enough to directly indicate in the remaining contents of the tube the somatic cell count which is the result of the test.

This is enabled because conversion of the data and calculations entered in the external table used were taken into consideration in the positioning of the graduation marks, with regard to the relationship between the measurement of the tube, its volume, the volume of its orifices, the distance between the marks, etc., thereby using analysis of data external to the tube itself.

Figure 2:
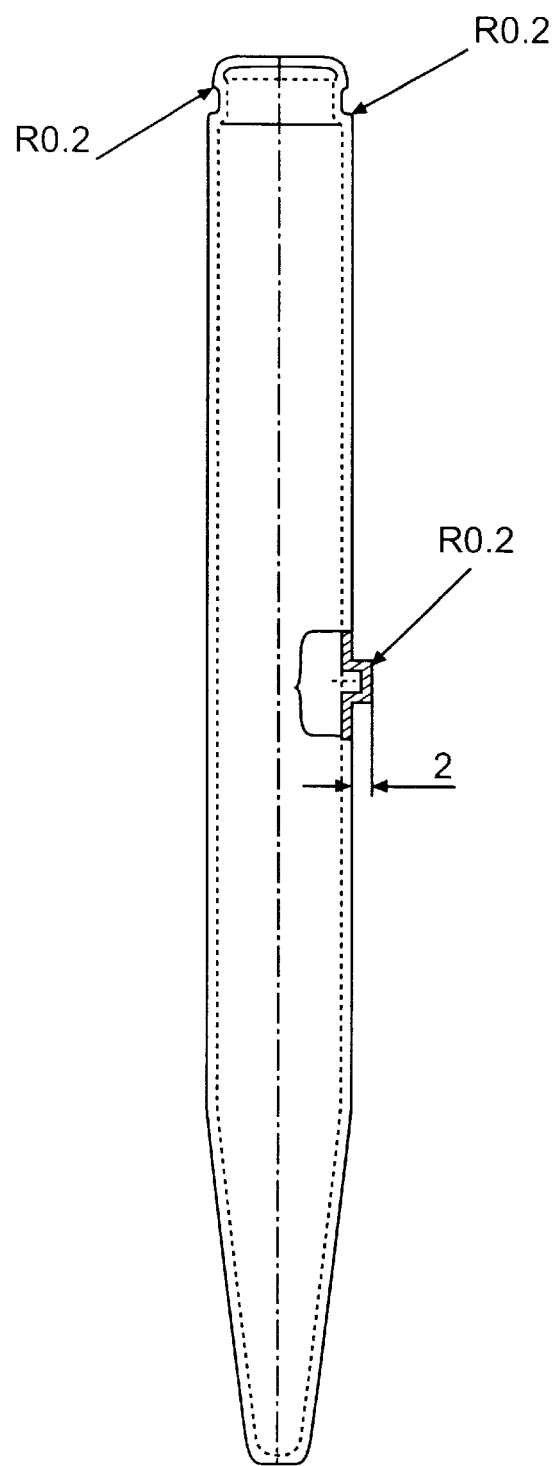
Figure 3:
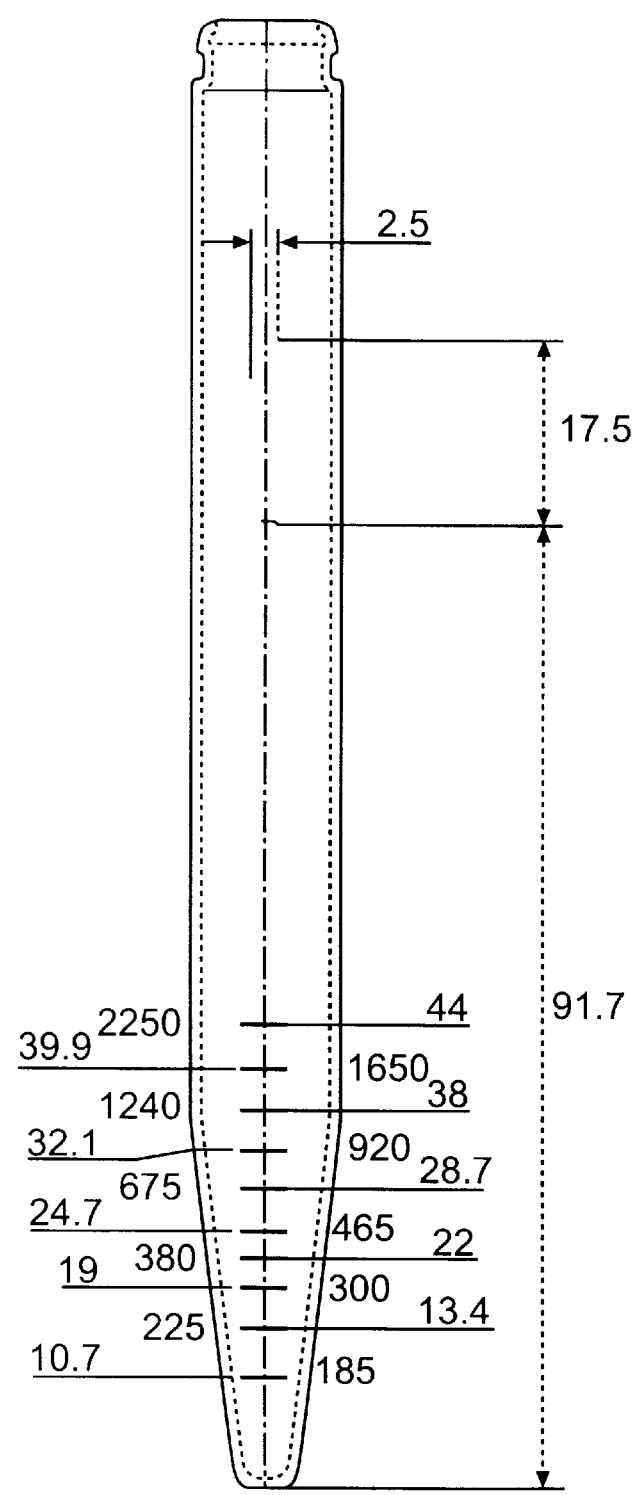

The attached diagrams show the layout of the tube with special scale intended for somatic cell count analysis tests of milk, said tube being the object of this patent, wherein the diagrams depict the following:

FIG. 1 shows a front view of the tube.
FIG. 2 shows a side view of the tube.
FIG. 3 shows a rear view of the tube.

In accordance with the drawings in the aforementioned figures, the model of a tube with special scale intended for tests which analyze somatic cell count in milk, which tube is the object of this patent, consists of a tube-shaped reservoir 130 mm high and 12.1 mm in diameter (inside)×140 mm (height) 1, closed at its bottom 2 and completely open at its top 3, with a 3-mm hole at a height of 78 mm, 4, made of polypropylene, with a scale graduated in thousands of somatic cells 5, arranged as follows:

| Scale in thousands of somatic cells | Height of scale in mm |
| --- | --- |
| <140 | 7.1 |
| 165 | 10.7 |
| 195 | 13.1 |
| 225 | 15.4 |
| 260 | 17.5 |
| 300 | 19.0 |
| 340 | 20.7 |
| 380 | 22.0 |
| 420 | 23.6 |
| 465 | 24.7 |
| 565 | 26.8 |
| 675 | 28.7 |
| 790 | 30.6 |
| 920 | 32.1 |
| 1,055 | 34.2 |
| 1,240 | 36.0 |
| 1,440 | 38.0 |
| 1,650 | 39.9 |
| 1,920 | 41.9 |
| 2,250 | 44.0 |
| >2,500 | 46.2 |

These divisions or scales are not linear, since they are the product of a correlation between residual volume and somatic cell count.

The opening at the top of the tube with special scale intended for tests which analyze somatic cell count in milk, which tube is the object of this utility model, is capped with a quickly adjustable and hermetically sealing lid (stopper 8), having a central hole with diameter of 1.09 to 1.10 mm 9, also made of high—density polyethylene plastic material.

Thus the tube operates in the same manner as the conventional ones used for somatic cell count analysis tests of milk, that is, a milk sample and suitable reagent are mixed inside the tube, then shaken and inverted for a certain period of time, to ensure that due to the air which enters via the lateral hole 4, gravity will cause leakage of a certain amount of the mixture through the orifice of the lid 9, thereby verifying, after returning to the original position, what the amount of the mixture remaining in the tube is.

After this has been done, simple observation of the scale graduated in thousands of somatic cells as printed on the tube 5 to which the amount of the mixture remaining in the tube corresponds, will reveal the test results, this being the innovation, improvement and industrial utility of the tube which is the object of this utility model.

Logically, the tube with a special scale intended for tests which analyze somatic cell count in milk, which tube is the object of this utility model, could be designed in different sample collection capacities and sizes, to meet the different needs of users of this type of test tube, but always with the scales, orifices and size of the tube being in proportion to one another.

Table of Correlations Between Volume in Milliliters and Somatic Cells

| Volume (ml) | Somatic cells | Volume (ml) | Somatic cells |
|---|---|---|---|
| 0.1 | 140,000 | 0.2 | 165,000 |
| 0.3 | 195,000 | 0.4 | 225,000 |
| 0.5 | 260,000 | 0.6 | 300,000 |
| 0.7 | 340,000 | 0.8 | 380,000 |
| 0.9 | 420,000 | 1.0 | 465,000 |
| 1.1 | 515,000 | 1.2 | 565,000 |
| 1.3 | 620,000 | 1.4 | 675,000 |
| 1.5 | 730,000 | 1.6 | 790,000 |
| 1.7 | 855,000 | 1.8 | 920,000 |
| 1.9 | 990,000 | 2.0 | 1,055,000 |
| 2.1 | 1,130,000 | 2.2 | 1,200,000 |
| 2.3 | 1,280,000 | 2.4 | 1,360,000 |
| 2.5 | 1,440,000 | 2.6 | 1,525,000 |
| 2.7 | 1,610,000 | 2.8 | 1,700,000 |
| 2.9 | 1,800,000 | 3.0 | 1,920,000 |
| 3.1 | 2,030,000 | 3.2 | 2,180,000 |
| 3.3 | 2,280,000 | — | — |

What is claimed is:

1. Tube with special scale intended for tests which analyze somatic cell count in milk, comprising a tube-shaped reservoir 130 mm high and 12.1 mm in diameter (inside)×140 mm (height) (1), closed at its bottom (2) and completely open at its top (3), with a 3-mm hole at a height of 78 mm (4), and having a quickly adjustable and hermetically sealing lid or stopper (8), having a central hole with diameter of 1.09 to 1.10 mm (9), also made of high-density polyethylene plastic material, wherein because a scale graduated in thousands of somatic cells (5) is printed on said tube, for the purpose of indicating in an automatic fashion directly on the tube itself the results of the test for which the tube was intended, said scales starting 5 mm from the bottom of the tube, this being the scale of least value (140 thousand cells per milliliter of milk) (6), the other scales laid out every 5 mm, with the scale of greatest value (2,280 thousand cells per milliliter of milk ) (7), located 40 mm from the bottom of the tube.

2. Tube according to claim 1, wherein the divisions or scales are not linear and are the product of a correlation between residual volume and somatic cell count.

* * * * *